(12) United States Patent
Diaz et al.

(10) Patent No.: US 7,753,931 B2
(45) Date of Patent: *Jul. 13, 2010

(54) EMBOLIC COIL INTRODUCER SYSTEM

(75) Inventors: Roberto Diaz, Miami, FL (US);
Mamdouh Elsakka, Warsaw, IN (US);
Boris Shkolnik, North Miami Beach, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 1238 days.

This patent is subject to a terminal disclaimer.

(21) Appl. No.: 11/166,314

(22) Filed: Jun. 24, 2005

(65) Prior Publication Data

US 2005/0234505 A1 Oct. 20, 2005

Related U.S. Application Data

(62) Division of application No. 10/250,845, filed as application No. PCT/US02/00897 on Jan. 10, 2002, now Pat. No. 7,018,394.

(60) Provisional application No. 60/260,742, filed on Jan. 10, 2001.

(51) Int. Cl.
*A61M 29/00* (2006.01)
(52) U.S. Cl. ............. 606/200; 606/108; 606/194; 623/1.11
(58) Field of Classification Search ............ 606/200, 606/108, 194; 623/1.11; 600/203
See application file for complete search history.

(56) References Cited

U.S. PATENT DOCUMENTS

| | | |
|---|---|---|
| 3,853,130 A | 12/1974 | Sheridan |
| 4,054,136 A | 10/1977 | von Zeppelin |
| 4,747,833 A | 5/1988 | Kousal et al. |
| 4,988,356 A | 1/1991 | Crittenden et al. |
| 4,997,424 A | 3/1991 | Little |
| 5,108,407 A | 4/1992 | Geremia et al. |
| 5,122,136 A | 6/1992 | Guglielmi et al. |
| 5,263,964 A | 11/1993 | Purdy |
| 5,334,210 A | 8/1994 | Gianturco |
| 5,350,397 A | 9/1994 | Palermo et al. |
| 5,380,290 A | 1/1995 | Makower et al. |
| 5,382,259 A | 1/1995 | Phelps et al. |
| 5,389,087 A | 2/1995 | Miraki |
| 5,601,600 A | 2/1997 | Ton |
| 5,817,123 A | 10/1998 | Kieturakis |
| 5,853,418 A | 12/1998 | Ken et al. |
| 6,063,100 A | 5/2000 | Diaz et al. |
| 6,113,622 A | 9/2000 | Hieshima |
| 6,117,142 A | 9/2000 | Goodson et al. |
| 6,179,857 B1 | 1/2001 | Diaz et al. |
| 6,183,491 B1 | 2/2001 | Lulo |
| 6,361,547 B1 | 3/2002 | Hieshima |
| 6,379,374 B1 | 4/2002 | Hieshima |
| 6,695,865 B2 | 2/2004 | Boyle |

*Primary Examiner*—(Jackie) Tan-Uyen T. Ho
*Assistant Examiner*—Jing Ou

(57) ABSTRACT

An apparatus and method for introducing a medical device deployment system into the vasculature of a human body and then using the deployment system for placing a medical device at a preselected position within a vessel, and an apparatus and method for introducing a medical device deployment system into the vasculature of a human body and then subsequently retrieving the deployment system, where the apparatus and method include an introducer having a detachable and reattachable sheath disposed about a deployment catheter.

28 Claims, 3 Drawing Sheets

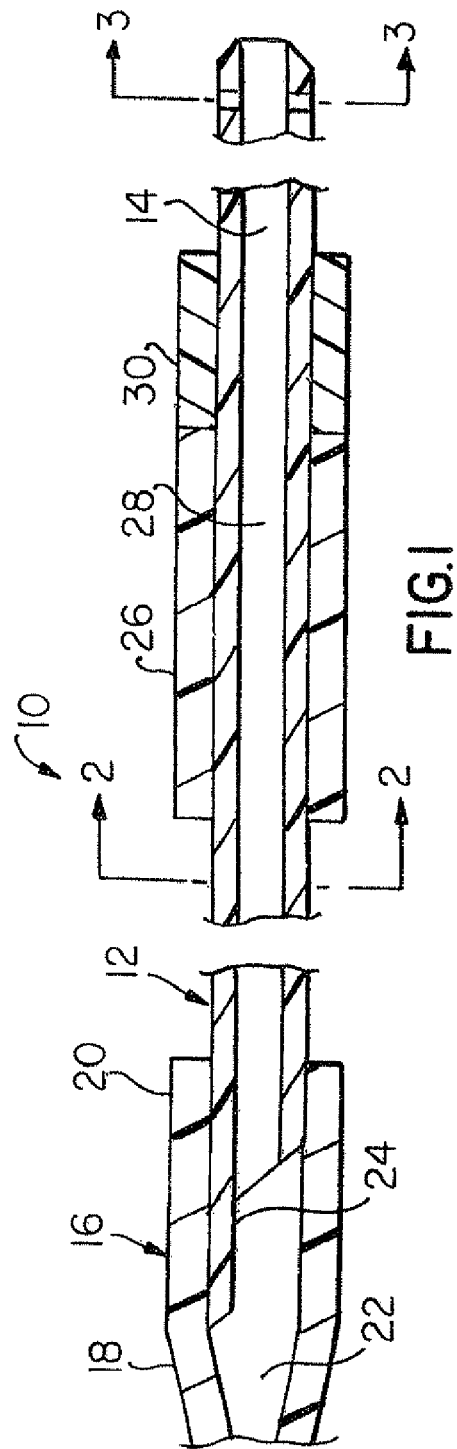
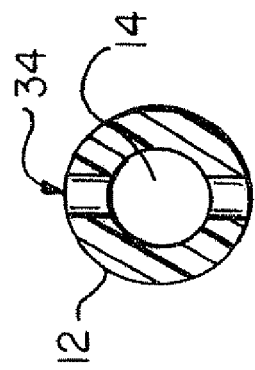
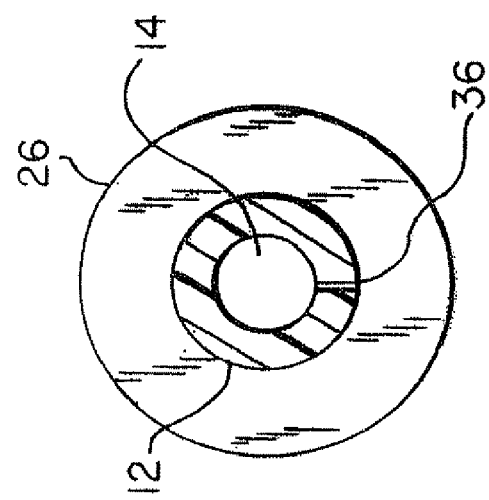

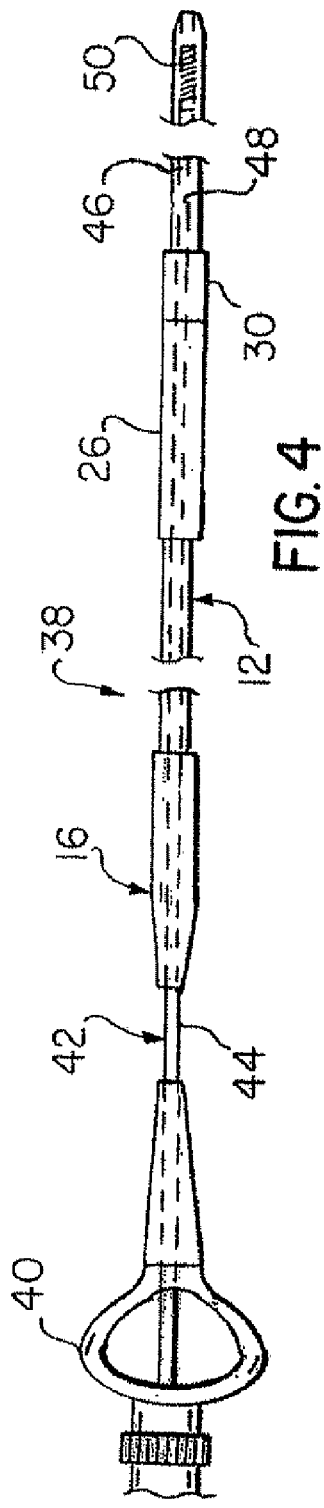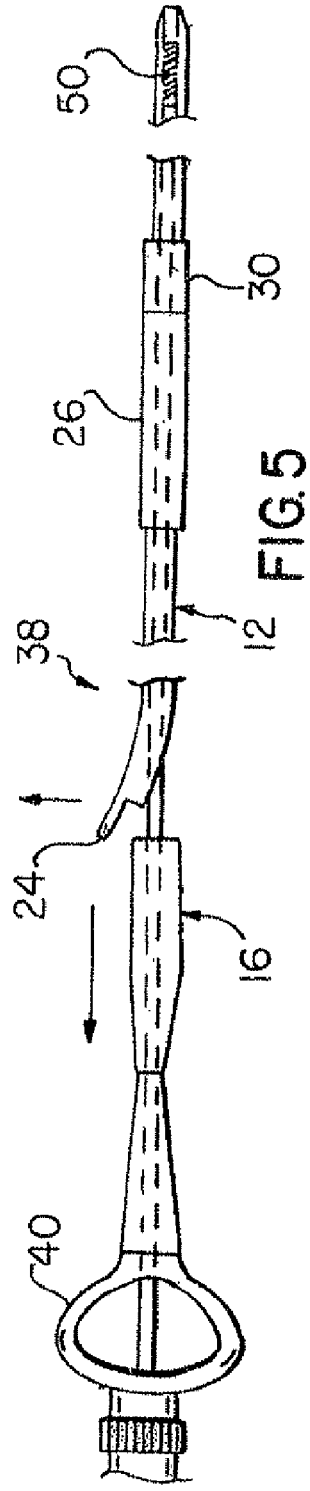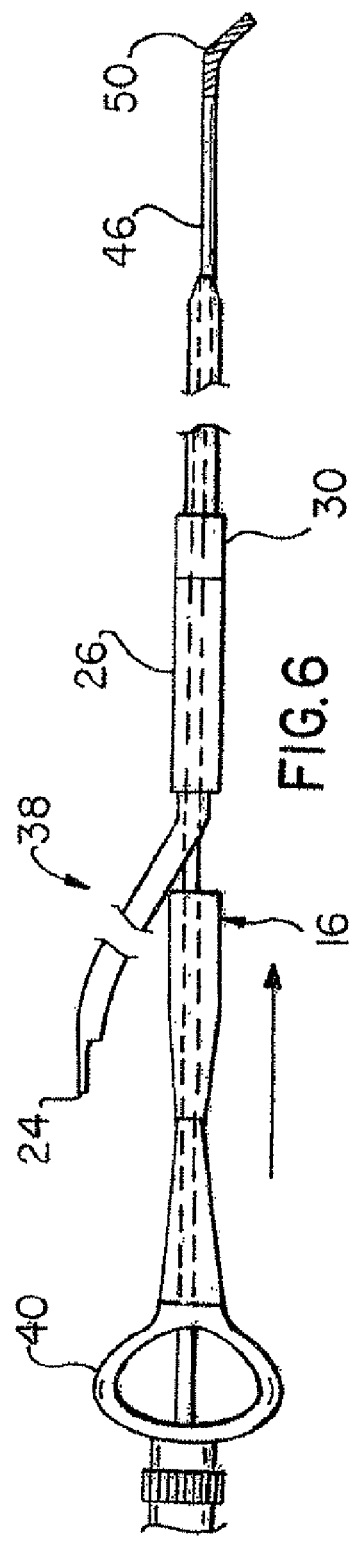

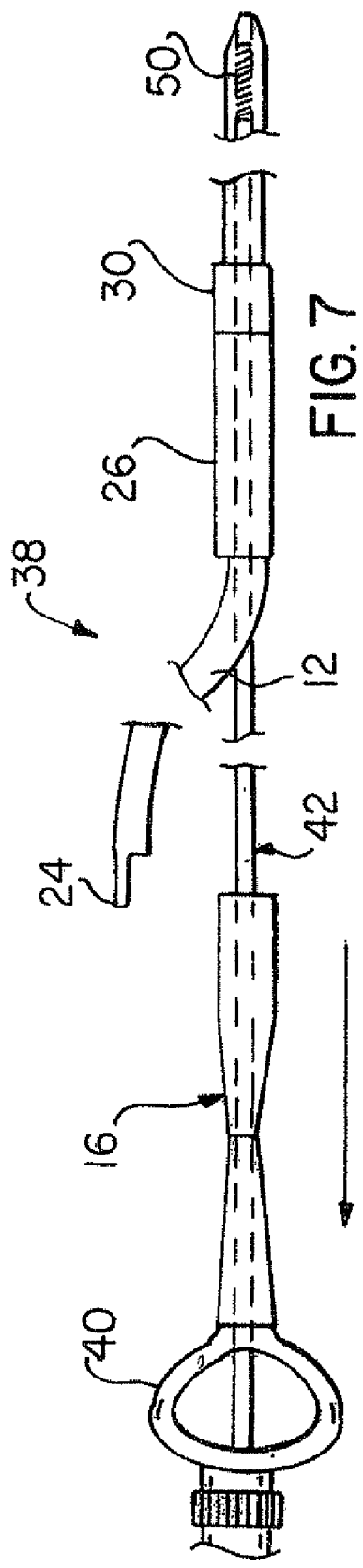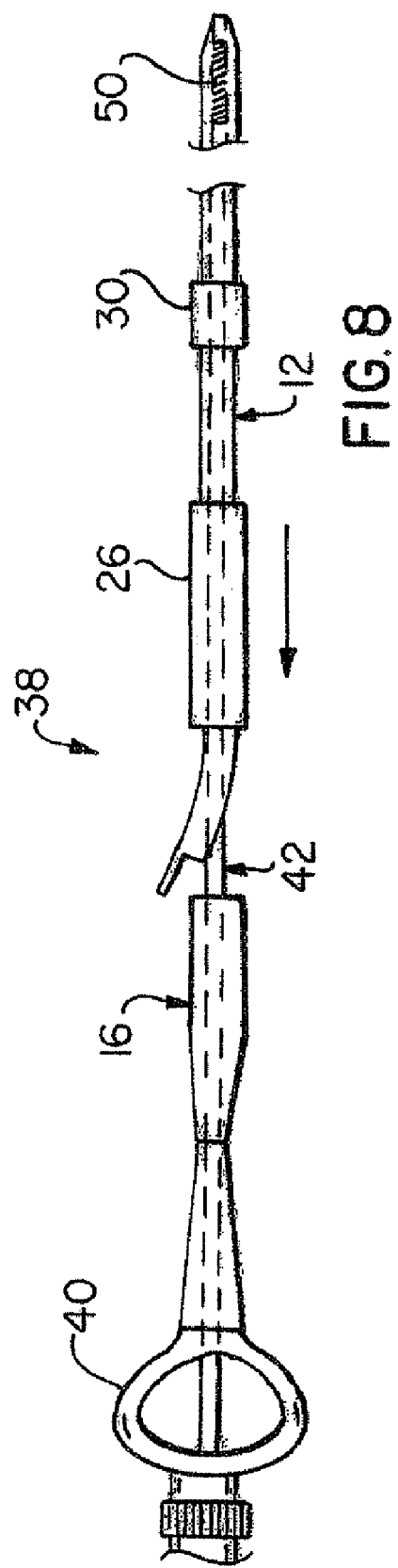

EMBOLIC COIL INTRODUCER SYSTEM

CROSS-REFERENCE TO RELATED APPLICATION

This patent application is a divisional patent application of U.S. patent application Ser. No. 10/250,845, filed on Dec. 8, 2003, (now U.S. Pat. No. 7,018,394), entitled, "Embolic Coil Introducer System", which claims priority of International Application Serial No. PCT/US02/00897, filed on Jan. 10, 2002, entitled, "Embolic Coil Introducer System", which claims priority of Provisional Patent Application Ser. No. 60/260,742, filed on Jan. 10, 2001, entitled, "Coil Sheath Introducer".

BACKGROUND OF THE INVENTION

1. Field of the Invention

This invention relates to an apparatus and method for introducing a medical device deployment system into the vasculature of a human body and then using the deployment system for placing a medical device at a preselected position within a vessel. The invention also relates to an apparatus and method for introducing a medical device deployment system into the vasculature of a human body and then subsequently retrieving the deployment system from the body. This apparatus and method are particularly suited for introducing an embolic coil deployment system into the tortuous vasculature of a human brain and then using the deployment system for placing an embolic coil within an aneurysm.

2. Description of the Prior Art

For many years physicians have been placing various devices within a blood vessel of the human body in order to treat an aneurysm or to occlude a vessel. Such devices are placed within the aneurysm or vessel using one of several catheter deployment systems. These deployment systems transport and release devices at a particular location within the vessel. The combination of different devices and deployment systems provide physicians with reliable methods of treating aneurysms.

Various types of devices are placed within an aneurysm or a vessel to occlude the flow of blood by promoting thrombus formation. Such devices include dilatation balloons, radiopaque fluids, liquid medications, and embolic coils. Embolic coils may take the form of helically wound coils, randomly wound coils, coils wound within other coils, or many other coil configurations. These coils are generally formed of radiopaque metallic materials, such as platinum, gold, and tungsten, or alloys of these metals. Often times, several coils are placed at a given location in order to occlude the flow of blood through the vessel.

One example of an embolic coil design is disclosed in U.S. Pat. No. 6,179,857 entitled, "Stretch Resistant Embolic Coil with Variable Stiffness." The coil is a helically wound coil in which various combinations of adjacent turns are spot welded together to create a stretch resistant coil of a preselected flexibility. Another coil configuration is disclosed in U.S. Pat. No. 6,183,491 entitled, "Embolic Coil Deployment System with Improved Embolic Coil" which shows an embolic coil having a relatively flexible proximal portion which resists stretching.

Also, U.S. Pat. No. 5,853,418 entitled "Stretch Resistant Vaso-occlusive Coils," discloses a helically wound coil having a polymeric stretch resistant member extending through the lumen of the coil and fixedly attached to both the distal end and the proximal end of the coil. Other examples of coil configurations are disclosed in U.S. Pat. No. 5,334,210, entitled, "Vascular Occlusion Assembly" and U.S. Pat. No. 5,382,259 entitled, "Vaso-occlusion Coil With Attached Tubular Woven Or Braided Fibrous Coverings". With all coil designs, it is important that embolic coils remain very flexible for traveling through vessels when used with catheter deployment systems.

A variety of deployment systems are available for placing embolic coils within an aneurysm or vessel. An example of such a system is disclosed in U.S. Pat. No. 6,113,622 entitled, "Embolic Coil Hydraulic Deployment System," assigned to the same assignee as the present patent application. The hydraulic embolic coil deployment system uses fluid pressure which is applied to the lumen of the deployment catheter for expanding the distal section radially to release the embolic coil at a preselected position.

Another coil deployment system utilizes a deployment catheter having a socket at the distal end for retaining a ball which is bonded to the proximal end of the coil. The ball is placed in the socket within the lumen at the distal end of the deployment catheter, and the deployment system is then moved into a vessel to place the coil at a desired position. Then, a pusher wire with a piston at the end is pushed distally from the proximal end of the deployment catheter to thereby push the ball out of the socket and release the coil at the desired position. This system is disclosed in U.S. Pat. No. 5,350,397 entitled, "Axially Detachable Embolic Coil Assembly."

Also, U.S. Pat. No. 5,263,964 entitled, "Coaxial Traction Detachment Apparatus and Method" discloses another coil deployment system. This system uses glue or solder for attaching an embolic coil to a guidewire which is, in turn, placed within a flexible deployment catheter for positioning the coil within the vessel at a preselected position. Once the coil is at the desired position, the coil is restrained by the deployment catheter, and the guidewire is pulled from the proximal end of the deployment catheter causing the coil to be detached from the guidewire and released from the deployment system.

Additionally, a small diameter vasoocclusive coil deployment system is disclosed in U.S. patent application Ser. No. 09/580,684 entitled, "Small Diameter Embolic Coil Hydraulic Deployment System," filed on May 30, 2000 and assigned to the same assignee as the present patent application. In this system, the distal end of a cylindrical headpiece is inserted into and bonded with an embolic coil. The proximal end of the cylindrical headpiece has a diameter approximately equal to the diameter of a lumen of a deployment catheter allowing the proximal end of the cylindrical headpiece to be disposed in fluid-tight engagement within the lumen of the distal section of the deployment catheter. When fluid pressure is applied to the lumen of the deployment catheter, the wall of the distal section of the deployment catheter expands radially and releases the cylindrical headpiece along with the embolic coil.

Examples of other deployment systems are disclosed in U.S. Pat. No. 5,122,136 entitled, "Endovascular Electrolytically Detachable Guidewire Tip For The Electroformation Of Thrombus In Arteries, Veins, Aneurysms, Vascular Malformations And Arteriovenous Fistulas" and U.S. Pat. No. 5,108,407 entitled, "Method And Apparatus For Placement Of An Embolic Coil."

SUMMARY OF THE INVENTION

In accordance with one aspect of the present invention, an embolic coil introducer system is provided for introducing a deployment catheter and embolic coil into the vasculature of a human body. The introducer system includes a deployment catheter and a vascular occlusive embolic coil attached to the catheter. The system also includes a sheath which takes the form of an elongated flexible tube and is disposed about the deployment catheter. The sheath has a longitudinal slit extending through a wall of the sheath. The sheath is detachable and reattachable such that when the end of the sheath is raised, the longitudinal slit is forced open and the sheath detaches from the deployment catheter. The introducer system also includes a stop which takes the form of a cylindrical member. The stop is fixedly disposed on the periphery of the sheath and is used to position the sheath while being inserted into the vasculature of the body. Finally, the introducer system includes a zipper which takes the form of a tubular member. The zipper is slideably disposed about the sheath such that when the zipper is moved proximally, the sheath is reattached onto the deployment catheter through the longitudinal slit.

In accordance with another aspect of the present invention, an embolic coil introducer is provided for introducing a deployment catheter and embolic coil into the vasculature of a human body. The introducer includes a detachable and reattachable sheath which takes the form of a flexible tube. The sheath has a longitudinal slit extending through the wall of the sheath. The sheath is detachable and reattachable such that when the end of the sheath is raised, the longitudinal slit is forced open and the sheath detaches from the deployment catheter. The introducer also includes a stop which takes the form of a cylindrical member. The stop is fixedly disposed on the periphery of the sheath and is used to position the sheath while being inserted into the vasculature of the body. Finally, the introducer includes a zipper which takes the form of a tubular member. The zipper is slideably disposed about the sheath such that when the zipper is moved proximally, the sheath is reattached onto the deployment catheter through the longitudinal slit.

In accordance with another aspect of the present invention, a medical device introducer system is provided for introducing a deployment catheter and medical device into the vasculature of a human body. The introducer system includes a deployment catheter and a medical device attached to the deployment catheter. The system also includes a sheath which is disposed about the deployment catheter. The sheath has a longitudinal slit extending through the wall of the sheath. The sheath is detachable and reattachable such that when the end of the sheath is raised, the longitudinal slit is forced open and the sheath detaches from the deployment catheter. The introducer system also includes a stop which takes the form of a cylindrical member. The stop is fixedly disposed on the periphery of the sheath and is used to position the sheath while being inserted into the vasculature of the body. Finally, the introducer system includes a zipper which takes the form of a tubular member. The zipper is slideably disposed about the sheath such that when the zipper is moved proximally, the sheath is reattached onto the deployment catheter through the longitudinal slit.

In accordance with a similar aspect of the present invention, a medical device introducer system is provided which includes a holder. The holder takes the form of a cylindrical member with a lumen and is slideably disposed about the sheath and deployment catheter so that the holder holds the sheath to the deployment catheter.

In accordance with a similar aspect of the present invention, a medical device introducer system is provided which includes a tapered holder. The tapered holder takes the form of a generally cylindrical member with a lumen and is slideably disposed about the sheath and deployment catheter so that the holder holds the sheath to the deployment catheter.

In accordance with a similar aspect of the present invention, a medical device introducer system is provided includes a tab extending from the proximal end of the sheath. The tab is positioned on the sheath generally on the opposite side of the longitudinal slit so that when the tab is lifted, the longitudinal slit is forced open and the sheath separates from the deployment catheter through the longitudinal slit.

In accordance with a similar aspect of the present invention, a medical device introducer system is provided which includes an integral tab formed by an integral member of the sheath. The tab is positioned on the sheath generally on the opposite side of the longitudinal slit so that when the tab is lifted, the longitudinal slit is forced open and the sheath separates from the deployment catheter through the longitudinal slit.

In accordance with a similar aspect of the present invention, a medical device introducer system is provided which includes a purge hole which takes the form of an opening in the wall of the sheath.

In accordance with a similar aspect of the present invention, a medical device introducer system is provided which includes a plurality of purge holes which take the form of openings in the wall of the sheath.

In accordance with another aspect of the present invention, a medical device introducer is provided for introducing a deployment catheter and medical device into the vasculature of a human body. The introducer includes a detachable and reattachable sheath which takes the form of a flexible tube. The sheath has a longitudinal slit extending through the wall of the sheath. The sheath is detachable and reattachable such that when the end of the sheath is raised, the longitudinal slit is forced open and the sheath detaches from the deployment catheter. The introducer also includes a stop which takes the form of a cylindrical member. The stop is fixedly disposed on the periphery of the sheath and is used to position the sheath while being inserted into the vasculature of the body. Finally, the introducer includes a zipper which takes the form of a tubular member. The zipper is slideably disposed about the sheath such that when the zipper is moved proximally, the sheath is reattached onto the deployment catheter through the longitudinal slit.

In accordance with a similar aspect of the present invention, a medical device introducer is provided which includes a holder. The holder takes the form of a cylindrical member with a lumen and is slideably disposed about the sheath and deployment catheter so that the holder holds the sheath to the deployment catheter.

In accordance with a similar aspect of the present invention, a medical device introducer is provided which includes a tapered holder. The tapered holder takes the form of a generally cylindrical member with a lumen and is slideably disposed about the sheath and deployment catheter so that the holder holds the sheath to the deployment catheter.

In accordance with a similar aspect of the present invention, a medical device introducer is provided which includes a tab extending from the proximal end of the sheath. The tab is positioned on the sheath generally on the opposite side of the longitudinal slit so that when the tab is lifted, the longitudinal slit is forced open and the sheath separates from the deployment catheter through the longitudinal slit.

In accordance with a similar aspect of the present invention, a medical device introducer is provided which includes an integral tab formed by an integral member of the sheath. The tab is positioned on the sheath generally on the opposite side of the longitudinal slit so that when the tab is lifted, the longitudinal slit is forced open and the sheath separates from the deployment catheter through the longitudinal slit.

In accordance with a similar aspect of the present invention, a medical device introducer is provided which includes a purge hole which takes the form of an opening in the wall of the sheath.

In accordance with a similar aspect of the present invention, a medical device introducer is provided which includes a plurality of purge holes which take the form of openings in the wall of the sheath.

In accordance with another aspect of the present invention, a method is provided for introducing an embolic coil deployment system into the vasculature of a human body and then using the deployment system for placing an embolic coil within an aneurysm. The method includes providing a delivery catheter, a deployment catheter, an embolic coil disposed within the deployment catheter, and an embolic coil introducer. The introducer includes a detachable and reattachable sheath disposed about the deployment catheter. The sheath has a longitudinal slit extending through the wall of the sheath. The introducer has a stop fixedly disposed on the periphery of the sheath and a zipper slideably disposed about the sheath. The method also includes inserting the delivery catheter into the vasculature of the human body and inserting the deployment catheter and the introducer into the delivery catheter. The method further includes raising the proximal end of the sheath slightly to expose the deployment catheter and moving the deployment catheter distally causing the sheath to detach from the deployment catheter through the longitudinal slit and causing the embolic coil to become exposed from the sheath. Finally, the method includes placing the embolic coil within the aneurysm then removing the deployment catheter, introducer, and delivery catheter from the body.

In accordance with another aspect of the present invention, a method is provided for introducing an embolic coil deployment system into the vasculature of a human body and then subsequently retrieving the deployment system from the vasculature of the body. The method includes providing a delivery catheter, a deployment catheter, an embolic coil disposed within the deployment catheter, and an embolic coil introducer. The introducer includes a detachable and reattachable sheath disposed about the deployment catheter. The sheath has a longitudinal slit extending through the wall of the sheath. The introducer has a stop fixedly disposed on the periphery of the sheath and a zipper slideably disposed about the sheath. The method also includes inserting the delivery catheter into the vasculature of the human body and inserting the deployment catheter and the introducer into the delivery catheter. The method further includes raising the proximal end of the sheath slightly to expose the deployment catheter and moving the deployment catheter distally causing the sheath to detach from the deployment catheter through the longitudinal slit and causing the embolic coil to become exposed from the sheath. The method also includes moving the deployment catheter proximally causing the embolic coil to retract into the sheath, then sliding the zipper proximally thereby causing the sheath to reattach about the deployment catheter through the longitudinal slit. Finally, the method includes removing the deployment catheter, introducer, and delivery catheter from the body.

In accordance with another aspect of the present invention, a method is provided for introducing a medical device deployment system into the vasculature of a human body and then using the deployment system for placing a medical device at a preselected position within a vessel. The method includes providing a delivery catheter, a deployment catheter, a medical device disposed within the deployment catheter, and a medical device introducer. The introducer includes a detachable and reattachable sheath disposed about the deployment catheter. The sheath has a longitudinal slit extending through the wall of the sheath. The introducer has a stop fixedly disposed on the periphery of the sheath and a zipper slideably disposed about the sheath. The method also includes inserting the delivery catheter into the vasculature of the human body and inserting the deployment catheter and the introducer into the delivery catheter. The method further includes raising the proximal end of the sheath slightly to expose the deployment catheter and moving the deployment catheter distally causing the sheath to detach from the deployment catheter through the longitudinal slit and causing the medical device to become exposed from the sheath. Finally, the method includes placing the medical device at the preselected position within the vessel then removing the deployment catheter, introducer, and delivery catheter from the body.

In accordance with another aspect of the present invention, a method is provided for introducing a medical device deployment system into the vasculature of a human body and then subsequently retrieving the deployment system from the vasculature of the body. The method includes providing a delivery catheter, a deployment catheter, a medical device disposed within the deployment catheter, and a medical device introducer. The introducer includes a detachable and reattachable sheath disposed about the deployment catheter. The sheath has a longitudinal slit extending through the wall of the sheath. The introducer has a stop fixedly disposed on the periphery of the sheath and a zipper slideably disposed about the sheath. The method also includes inserting the delivery catheter into the vasculature of the human body and inserting the deployment catheter and the introducer into the delivery catheter. The method further includes raising the proximal end of the sheath slightly to expose the deployment catheter and moving the deployment catheter distally causing the sheath to detach from the deployment catheter through the longitudinal slit and causing the medical device to become exposed from the sheath. The method also includes moving the deployment catheter proximally causing the medical device to retract into the sheath then sliding the zipper proximally thereby causing the sheath to reattach about the deployment catheter through the longitudinal slit. Finally, the method includes removing the deployment catheter, introducer, and delivery catheter from the body.

These aspects of the invention and the advantages thereof will be more clearly understood from the following description and drawings of the preferred embodiment.

BRIEF DESCRIPTION OF THE DRAWINGS

FIG. 1 is an enlarged, sectional view of an introducer in accordance with the present invention;

FIG. 2 is an enlarged, cross-sectional view of the introducer of FIG. 1 viewed along the line 2-2 showing a longitudinal slit in a wall of a sheath;

FIG. 3 is an enlarged, cross-sectional view of the sheath of FIG. 1 viewed along the line 3-3 showing purge holes;

FIG. 4 is an enlarged view of an introducer system showing the introducer disposed about a deployment catheter with an embolic coil;

FIG. 5 is an enlarged perspective view of the introducer system showing a holder being moved proximally along the deployment catheter and a tab being lifted causing the sheath to separate from the deployment catheter;

FIG. 6 is an enlarged perspective view of the introducer system showing the deployment catheter and holder being moved distally, forcing the sheath off the deployment catheter and forcing an embolic coil out the end of the sheath;

FIG. 7 is an enlarged perspective view of the introducer system showing the deployment catheter and holder being moved proximally, pulling the embolic coil back into the sheath; and, FIG. 8 is an enlarged perspective view of the introducer system showing a zipper being moved proximally, forcing the sheath back onto the deployment catheter.

DESCRIPTION OF THE PREFERRED EMBODIMENT

FIG. 1 illustrates an introducer 10 which includes a sheath 12 having a lumen 14. The sheath 12 is approximately 80 centimeters in length and is formed of a polymer material with a durometer in the range of about 50 D and 70 D. The sheath 12 has a diameter of approximately 0.1 centimeters, and the lumen 14 of the sheath 12 has a diameter slightly greater than an outside diameter of a deployment catheter 44. The sheath 12 includes a longitudinal slit 34 in the wall of the sheath 12. The slit 34 is approximately 60 centimeters in length and extends from the proximal end of the sheath 12 to a position intermediate the proximal and distal ends of the sheath 12. The sheath 12 also includes an integral tab 24 at the proximal end of the sheath 12. The integral tab 24 is made of a polymer material and is approximately 2 centimeters in length. Finally, the sheath 12 includes purge holes 36 at the distal end of the sheath 12. The purge holes 36 can vary in diameter but preferably the holes 36 have a diameter of approximately 0.02 centimeters.

The introducer 10 also includes a holder 16 having a lumen 22. The holder 16 is slideably disposed about the proximal end of the sheath 12. The holder 16 is made from polyethylene but can be formed from other material like plastic or a polymer. The holder 16 is generally cylindrical in shape, but the proximal section 18 is tapered. The outside diameter of the proximal section 18 is approximately 0.07 centimeters while the diameter of the distal section 20 is approximately 0.1 centimeters. The holder 16 has a length of approximately 11.5 centimeters. A stop 30 is attached to the periphery of the sheath 12 at an intermediate position along the sheath 12. The stop 30 is cylindrical in shape and is made of nylon but can also be formed from plastic or a polymer. The length of the stop 30 is approximately 1.3 centimeters while the diameter of the stop 30 can vary but the preferred diameter is 0.18 centimeters. A zipper 26 is slide ably disposed about the sheath 12 and is approximately 4.5 centimeters in length. The zipper 26 is generally cylindrical in shape and has a lumen 28. The zipper 26 is formed of polyethylene but can also be made from plastic or a polymer. The lumen 28 of the zipper 26 has a diameter slightly greater than the outside diameter of the sheath 12. The outside diameter of the zipper 26 can vary but the preferred diameter is 0.18 centimeters.

FIG. 2 illustrates a cross sectional view of the sheath 12 between the holder 16 and the zipper 26. The longitudinal slit 34 runs completely through the wall of the sheath 12. The zipper 26 is slideably disposed about the sheath 12.

FIG. 3 illustrates a cross sectioned view of the sheath 12 between the stop 30 and the distal end of the sheath 12. Purge holes 36 extend through the wall of the sheath 12.

FIG. 4 illustrates an introducer system 38 which includes the introducer 10 slideably disposed about a deployment catheter 42. The deployment catheter 42 is an elongated tube with a lumen 48. Preferably, the proximal section 44 of the deployment catheter 42 is formed of pellethane material having a durometer in a range of about 60D to 75D. The proximal section 44 is sufficiently flexible to transverse the vasculature of the human body, but is sufficiently rigid so that it can be pushed distally through the sheath 12. The distal section 46 of the deployment catheter 42 is preferably formed of a pellethane material having a durometer of between 25D and 55D with a durometer of 40D being the preferred durometer.

The introducer system 38 also includes a winged hub 40 coupled to the proximal section 44 of a deployment catheter 42. The winged hub 40 is made from plastic and aids in the insertion of the deployment catheter 42 into the vascular of the body. Furthermore, the system 38 includes an embolic coil 50 attached to the deployment catheter 42 and disposed within the sheath 12 of the introducer 10. The embolic coil 50 may take various forms and configurations and may even take the form of a randomly wound coil, however, a helically wound flexible embolic coil 50 is illustrated in FIG. 4.

FIG. 5 illustrates the holder 16 being moved proximally to expose the integral tab 24. The integral tab 24 is raised slightly, forcing the proximal end of the sheath 12 to separate from the deployment catheter 42 through the longitudinal slit 36.

FIG. 6 illustrates the winged hub 40, the deployment catheter 42, and the holder 16 being moved distally, forcing the sheath 12 to separate from the deployment catheter 42 through the longitudinal slit 36 and pushing the embolic coil 50 out the distal end of the sheath 12.

FIG. 7 illustrates the winged hub 40, the deployment catheter 42, and the holder 16 being moved proximally, pulling the embolic coil 50 back into the distal end of the sheath 12.

FIG. 8 illustrates the zipper 26 being moved proximally over the sheath 12 causing the sheath to reattach about the deployment catheter 42 through the longitudinal slit 36.

The embolic coil introducer system operates to introduce a deployment catheter and embolic coil into the vasculature of the human body. With the introducer slideably disposed over the deployment catheter, the holder is positioned over the integral tab causing the introducer to be held to the deployment catheter. In this configuration, the system can be inserted into a delivery catheter. The sheath of the introducer protects the embolic coil as the distal end of the system is inserted into the patient. At this point, the holder is moved proximally to expose the integral tab. Then, the integral tab is raised slightly to begin separating the sheath from the deployment catheter through the longitudinal slit. To continue separating the sheath, the deployment catheter and holder are moved distally which forces the remaining part of the sheath off the deployment catheter. The sheath allows the deployment catheter to enter the vasculature more easily; otherwise, the flexible deployment catheter would bend as it was being pushed distally. At the same time the sheath is separating from the deployment catheter, the embolic coil attached to the distal end of the catheter exits the sheath.

From this position, the physician can deploy the embolic coil at a preselected position within a vessel. Once the coil is no longer attached to the deployment catheter, the system is removed from the vasculature and another system is introduced in the same manner when more coils are required.

If, before the embolic coil is deployed, the physician decides to retrieve the coil, the sheath can be reattached, and the system can be reused. To do this, the deployment catheter is pulled proximally until the coil is again disposed within the sheath. Then, the zipper is slid from the stop to the holder, reattaching the sheath onto the deployment catheter through the longitudinal slit. The holder is then slid over the integral tab to hold the sheath to the deployment catheter. Finally, the system is removed from the patient.

A novel system has been disclosed in which a deployment catheter and embolic coil are introduced into the vasculature of the body. Although a preferred embodiment of the invention has been described, it is to be understood that various modifications may be made by those skilled in the art without departing from the scope of the present invention. For example, there are many variations and modifications of the embolic coil, including numerous coil winding configurations, or alternatively, other types of vascular occlusive devices may be utilized, such as dilation balloons, radiopaque fluids, and liquid medications.

These and other modifications would be apparent to those having ordinary skill in the art to which this invention relates and are intended to be within the scope of the claims which follow.

That which is claimed is:

1. An embolic coil introducer system for introducing a deployment catheter and an embolic coil into the vasculature of a body, said introducer system comprising:
   a deployment catheter which takes the form of an elongated flexible tube having a lumen extending therethrough and having a proximal section and a distal section;
   a detachable and reattachable sheath which takes the form of a flexible tube having a lumen extending therethrough, said sheath having a proximal end and a distal end, said sheath having a longitudinal slit extending through a wall of said sheath and extending from the proximal end to a position intermediate the proximal and distal ends, said sheath being disposed about said deployment catheter through said lumen of said sheath, and said sheath being detachable and reattachable such that when the proximal end of said sheath is raised, said longitudinal slit is forced open and said sheath detaches and reattaches from said deployment catheter through said longitudinal slit;
   a vascular occlusive embolic coil being attached to the distal section of said deployment catheter, said embolic coil being disposed within the lumen of said sheath;
   a stop which takes the form of a cylindrical member having a lumen extending therethrough, said lumen of said cylindrical member having a diameter approximately equal to an outside diameter of said sheath, said stop fixedly disposed on the periphery of said sheath at the position intermediate the proximal and distal ends of said sheath, and said stop being used to position said sheath while being inserted into the vasculature of the body; and
   a zipper which takes the form of a tubular member having a lumen extending therethrough, said lumen of said zipper having a diameter approximately equal to an outside diameter of said sheath, said zipper being slideably disposed about said sheath between the proximal end of said sheath and the position intermediate the proximal and distal ends of said sheath such that when said zipper is moved proximally, said sheath is reattached onto said deployment catheter through said longitudinal slit.

2. An embolic coil introducer system as defined in claim 1, wherein said introducer system includes a holder which takes the form of a generally cylindrical member having a lumen extending therethrough and having a proximal section and a distal section, the lumen at the distal section of said holder having a diameter approximately equal to an outside diameter of said sheath, the lumen at the proximal section of said holder having a diameter approximately equal to an outside diameter of said deployment catheter, the distal section of said holder being slideably disposed about the proximal end of said sheath so that said holder holds said sheath to said catheter, the proximal section of said holder being slideably disposed about 20 the proximal section of said deployment catheter such that when said holder is moved proximally along said catheter, the proximal end of said sheath becomes exposed.

3. An embolic coil introducer system as defined in claim 2, wherein the holder takes the form of a generally cylindrical member having a tapered proximal section.

4. An embolic coil embolic coil introducer system as defined in claim 1, wherein said introducer system includes a tab which takes the form of a projection extending from the proximal end of said sheath from a position generally on the opposite side of said sheath from the longitudinal slit so that when said tab is lifted, said longitudinal slit is forced open and said sheath separates from said deployment catheter through said longitudinal slit.

5. An embolic coil introducer system as defined in claim 4, wherein said tab takes the form of an integral tab having an integral member of said sheath extending from the proximal end of said sheath.

6. An embolic coil introducer system as defined in claim 1, wherein said introducer system includes a purge hole which takes the form of an opening in a wall of said sheath.

7. An embolic coil introducer system as defined in claim 6, wherein said introducer system includes purge holes which take the form of a plurality of openings in the wall of said sheath.

8. An embolic coil introducer for introducing a deployment catheter and an embolic coil into the vasculature of a body, said introducer comprising:
   a detachable and reattachable sheath which takes the form of a flexible tube having a lumen extending therethrough, said sheath having a proximal end and a distal end, said sheath having a longitudinal slit extending through a wall of said sheath and extending from the proximal end to the position intermediate the proximal and distal ends, said sheath being disposed about a deployment catheter through said lumen of said sheath, and said sheath being detachable such that when the proximal end of said sheath is raised, said longitudinal slit is forced open and said sheath detaches from said deployment catheter through said longitudinal slit; a stop which takes the form of a cylindrical member having a lumen extending therethrough, said lumen in said stop having a diameter approximately equal to an outside diameter of said sheath, said stop fixedly disposed on the periphery of said sheath at the position intermediate the proximal and distal ends of said sheath, and 15 said stop being used to position said sheath while being inserted into the vasculature of the body; and
   a zipper which takes the form of a tubular member having a lumen extending therethrough, said lumen in said zipper having a diameter approximately equal to an outside diameter of said sheath, said zipper being slideably disposed about said sheath between the proximal end of said sheath and the position intermediate the proximal and distal ends of said sheath such that when said zipper is moved proximally, said sheath is reattached onto said deployment catheter through said longitudinal slit.

9. An embolic coil introducer as defined in claim 8, wherein said introducer includes a holder which takes the form of a generally cylindrical member having a lumen extending therethrough and having a proximal section and a distal section, the lumen at the distal section of said holder having a diameter approximately equal to an outside diameter of said sheath, the lumen at the proximal section of said holder having a diameter approximately equal to an outside diameter of said deployment catheter, the distal section of said holder being slideably disposed about the proximal end of said sheath so that said holder holds said sheath to said deployment catheter, the proximal section of said holder being slideably disposed about the proximal section of said deployment catheter such that when said holder is moved proximally along said catheter, the proximal end of said sheath becomes exposed.

10. An embolic coil introducer as defined in claim 9, wherein said holder takes the form of a generally cylindrical member having a tapered proximal section.

11. An embolic coil introducer as defined in claim 8, wherein said introducer includes a tab which takes the form of a member extending from the proximal end of said sheath from a position on said sheath generally on the opposite side of said longitudinal slit so that when said tab is lifted, said longitudinal slit is forced open and said sheath separates from said deployment catheter through said longitudinal slit.

12. An embolic coil introducer as defined in claim 11, wherein said tab takes the form of an integral tab having an integral member of said sheath extending from the proximal end of said sheath.

13. An embolic coil introducer as defined in claim 1, wherein the introducer includes a purge hole which takes the form of an opening in a wall of said sheath.

14. An embolic coil introducer as defined in claim 6, wherein the introducer includes purge holes which take the form of a plurality of openings in the wall of said sheath.

15. A medical device introducer system for introducing a deployment catheter and medical device into the vasculature of a body, said introducer system comprising:
   a deployment catheter which takes the form of an elongated flexible tube having a lumen extending therethrough and having a proximal section and a distal section;
   a detachable and reattachable sheath which takes the form of a flexible tube having a lumen extending therethrough, said sheath having a proximal end and a distal end, said sheath having a longitudinal slit extending through a wall of said sheath and extending from the proximal end to the position intermediate the proximal and distal ends, said sheath being disposed about said deployment catheter through said lumen of said sheath, and said sheath being detachable such that when the proximal end of said sheath is raised, said longitudinal slit is forced open and said sheath detaches from said deployment catheter through said longitudinal slit;
   a vascular occlusive medical device being attached to the distal section of said deployment catheter, said medical device being disposed within the lumen of said sheath;
   a stop which takes the form of a cylindrical member having a lumen extending therethrough, said lumen in said stop having a diameter approximately equal to an outside diameter of said sheath, said stop fixedly disposed on the periphery of said sheath at the position intermediate the proximal and distal ends of said sheath, and said stop being used to position said sheath while being inserted into the vasculature of the body; and
   a zipper which takes the form of a tubular member having a lumen extending therethrough, said lumen in said zipper having a diameter approximately equal to an outside diameter of said sheath, said zipper being slideably disposed about said sheath between the proximal end of said sheath and the position intermediate the proximal and distal ends of said sheath such that when said zipper is moved proximally, said sheath is reattached onto said deployment catheter through said longitudinal slit.

16. A medical device introducer system as defined in claim 15, wherein said introducer system includes a holder which takes the form of a generally cylindrical member having a lumen extending therethrough and having a proximal section and a distal section, the lumen at the distal section of said holder having a diameter approximately equal to an outside diameter of said sheath, the lumen at the proximal section of said holder having a diameter approximately equal to an outside diameter of said deployment catheter, the distal section of said holder being slideably disposed about the proximal end of said sheath so that said holder holds said sheath to said deployment catheter, the proximal section of said holder being slideably disposed about the proximal section of said deployment catheter such that when said holder is moved proximally along said catheter, the proximal end of said sheath becomes exposed.

17. A medical device introducer system as defined in claim 16, wherein said holder takes the form of a generally cylindrical member having a tapered proximal section.

18. A medical device introducer system as defined in claim 15, wherein said introducer system includes a tab which takes the form of a projection extending from the proximal end of said sheath from a position generally on the opposite side of said sheath from said longitudinal slit so that when said tab is lifted, said longitudinal slit is forced open and said sheath separates from said deployment catheter through said longitudinal slit.

19. A medical device introducer system as defined in claim 18, wherein said tab takes the form of an integral tab having an integral member of said sheath extending from the proximal end of said sheath.

20. A medical device introducer system as defined in claim 15, wherein said introducer system includes a purge hole which takes the form of an opening in a wall of said sheath.

21. A medical device introducer system as defined in claim 20, wherein said introducer system includes purge holes which take the form of a plurality of openings in a wall of said sheath.

22. A medical device introducer for introducing a deployment catheter and a medical device into the vasculature of a body, said introducer comprising:
   a detachable and reattachable sheath which takes the form of a flexible tube having a lumen extending therethrough, said sheath having a proximal end and a distal end, said sheath having a longitudinal slit extending through a wall of said sheath and extending from the proximal end to the position intermediate the proximal and distal ends, said sheath being disposed about said deployment catheter through said lumen of said sheath, and said sheath being detachable such that when the proximal end of said sheath is raised, said longitudinal slit is forced open and said sheath detaches from said deployment catheter through said longitudinal slit; a stop which takes the form of a cylindrical member having a lumen extending therethrough, said lumen in said stop having a diameter approximately equal to an outside diameter of said sheath, said stop fixedly disposed on the periphery of said sheath at the position intermediate the proximal and distal ends of said sheath, and said stop being used to position said sheath while being inserted into the vasculature of the body; and
   a zipper which takes the form of a tubular member having a lumen extending therethrough, said lumen in said zipper having a diameter approximately equal to an outside diameter of said sheath, said zipper being slideably disposed about said sheath between the proximal end of said sheath and the position intermediate the proximal and distal ends of said sheath such that when said zipper is moved proximally, said sheath is reattached onto said deployment catheter through said longitudinal slit.

23. A medical device introducer as defined in claim 22, wherein said introducer includes a holder which takes the form of a generally cylindrical member having a lumen extending therethrough and having a proximal section and a distal section, the lumen at the distal section of said holder having a diameter approximately equal to an outside diameter of said sheath, the lumen at the proximal section of said holder having a diameter approximately equal to an outside diameter of said deployment catheter, the distal section of said holder being slideably disposed about the proximal end of said sheath so that said holder holds said sheath to said deployment catheter, the proximal section of said holder being slideably disposed about the proximal section of said deployment catheter such that when said holder is moved proximally along said catheter, the proximal end of said sheath becomes exposed.

24. A medical device introducer as defined in claim 23, wherein said holder takes the form of a generally cylindrical member having a tapered proximal section.

25. A medical device introducer as defined in claim 22, wherein said introducer includes a tab which takes the form of a projection extending from the proximal end of said sheath from a position generally on the opposite side of said sheath from said longitudinal slit so that when said tab is lifted, said longitudinal slit is forced open and said sheath separates from said deployment catheter through said longitudinal slit.

26. A medical device introducer as defined in claim 23, wherein said tab takes the form of an integral tab having an integral member of said sheath extending from the proximal end of said sheath.

27. A medical device introducer as defined in claim 22, wherein said introducer includes a purge hole which takes the form of an opening in a wall of said sheath.

28. A medical device introducer as defined in claim 27, wherein said introducer includes purge holes which take the form of a plurality of openings in said wall of said sheath.

* * * * *